United States Patent
Mo et al.

(10) Patent No.: US 12,187,292 B2
(45) Date of Patent: Jan. 7, 2025

(54) RISKY DRIVING PREDICTION METHOD AND SYSTEM BASED ON BRAIN-COMPUTER INTERFACE, AND ELECTRONIC DEVICE

(71) Applicant: HONG KONG PRODUCTIVITY COUNCIL, Hong Kong (HK)

(72) Inventors: Tiande Mo, Hong Kong (HK); Yao Liu, Hong Kong (HK); Chi Kin Poon, Hong Kong (HK); Yu Li, Hong Kong (HK)

(73) Assignee: HONG KONG PRODUCTIVITY COUNCIL, Hong Kong (HK)

( * ) Notice: Subject to any disclaimer, the term of this patent is extended or adjusted under 35 U.S.C. 154(b) by 263 days.

(21) Appl. No.: 17/697,815

(22) Filed: Mar. 17, 2022

(65) Prior Publication Data
US 2023/0271617 A1  Aug. 31, 2023

Related U.S. Application Data

(60) Provisional application No. 63/314,211, filed on Feb. 25, 2022.

(51) Int. Cl.
*B60W 40/09* (2012.01)
*A61B 5/18* (2006.01)
(Continued)

(52) U.S. Cl.
CPC ........... *B60W 40/09* (2013.01); *A61B 5/18* (2013.01); *A61B 5/369* (2021.01); *B60R 25/04* (2013.01);
(Continued)

(58) Field of Classification Search
None
See application file for complete search history.

(56) References Cited

U.S. PATENT DOCUMENTS

2004/0044293 A1* 3/2004 Burton ............... B60T 7/12
600/544
2008/0319602 A1* 12/2008 McClellan ......... G07C 5/085
701/31.4
(Continued)

FOREIGN PATENT DOCUMENTS

KR         101548868 B1 *  9/2015

OTHER PUBLICATIONS

Google English Translation of KR 101548868 B1 (Year: 2015).*
Merged Foreign Document and PE2E English Translation of WO 2020147235 A1 (Year: 2020).*

*Primary Examiner* — Justin S Lee
*Assistant Examiner* — Andrew Sang Kim
(74) *Attorney, Agent, or Firm* — Maschoff Brennan

(57) ABSTRACT

The present invention provides a risky driving prediction method and system based on a brain-computer interface, and an electronic device. The risky driving prediction method based on the brain-computer interface includes: performing, by a driver, at least one responsiveness test item before starting a vehicle; applying a brain-computer interface to acquire an electroencephalogram signal of the driver performing the at least one responsiveness test item, and analyzing the electroencephalogram signal to generate feedback information; and analyzing the feedback information based on a preset test standard to determine whether the driver has a risky driving behavior. Therefore, by using the risky driving prediction method, it can be detected whether the driver is in a state suitable for driving the vehicle without requiring the driver to do any body movement or language response.

12 Claims, 4 Drawing Sheets

(51) Int. Cl.
*A61B 5/369* (2021.01)
*B60R 25/04* (2013.01)
(52) U.S. Cl.
CPC ... *B60W 2540/221* (2020.02); *B60W 2540/24* (2013.01)

(56) References Cited

U.S. PATENT DOCUMENTS

| | | | | |
|---|---|---|---|---|
| 2009/0090577 | A1* | 4/2009 | Takahashi | G01N 33/4972 |
| | | | | 340/576 |
| 2012/0228047 | A1* | 9/2012 | White | B60K 28/063 |
| | | | | 180/272 |
| 2019/0307350 | A1* | 10/2019 | Sridhar | A61B 5/4082 |
| 2020/0029880 | A1* | 1/2020 | Katnani | A61B 5/4064 |
| 2020/0241525 | A1* | 7/2020 | Harbour | G05D 1/0061 |

* cited by examiner

RISKY DRIVING PREDICTION METHOD AND SYSTEM BASED ON BRAIN-COMPUTER INTERFACE, AND ELECTRONIC DEVICE

TECHNICAL FIELD

The present invention relates to the technical field of safe driving of vehicles, in particular to a risky driving prediction method and system based on a brain-computer interface, and an electronic device.

BACKGROUND ART

In modern society, with the increment of car ownership and the increasing expansion of road construction scales, the traffic safety problem also becomes more and more obvious. A risky driving behavior, such as drunk driving, fatigue driving and medicine effects, of a driver will undoubtedly bring huge potential safety hazards to the driver, passengers and pedestrians on a road. At present, although many monitoring technologies such as monitoring an alcohol content of air in a vehicle, monitoring components of sweat in the palm of the driver, tracking eyeball movement of the driver and monitoring an eyelid blinking frequency have been provided to predict the risky driving behavior in advance, the above-mentioned monitoring technologies are indirect monitoring which has the problems such as unscientific monitoring objective indexes and nonideal monitoring results caused by external environmental factor disturbance. For example, if the driver wears a shelter such as a gauze mask or gloves or takes fermented food to cause false triggering, such detection is lower in accuracy.

Therefore, how to directly, accurately and objectively monitor the responsiveness and judgment of the driver before driving to avoid a risky driving behavior of the driver in a fatigue state or under the effect of wines or drugs so as to prevent the driver from causing driving violation and even traffic accidents due to incapability of appropriately controlling a vehicle has become one of important research topics in the technical field of safety driving of vehicles.

SUMMARY OF THE INVENTION

The technical problem to be solved by the present invention is to determine whether a driver is currently in a state suitable for driving a vehicle by directly, accurately and objectively monitoring the current responsiveness and judgment of the driver before the vehicle is started so that harm caused by a risky driving behavior of the driver is avoided.

In order to solve the above-mentioned technical problem, the present invention provides a risky driving prediction method based on a brain-computer interface, including the steps: performing, by a driver, at least one responsiveness test item before starting a vehicle; applying a brain-computer interface to acquire an electroencephalogram signal of the driver performing the at least one responsiveness test item, and analyzing the electroencephalogram signal to generate feedback information; and analyzing the feedback information based on a preset test standard to determine whether the driver has a risky driving behavior.

In order to solve the above-mentioned technical problem, the present invention further provides a risky driving prediction system based on a brain-computer interface, including a test module, an information acquisition and analysis module and a processor module, wherein each of the test module and the information acquisition and analysis module is electrically connected with the processor module; the test module acquires a responsiveness test item and test interaction information of a driver by virtue of the processor module so as to test the driver; the information acquisition and analysis module acquires an electroencephalogram signal of the driver being tested and analyzes the electroencephalogram signal so as to generate feedback information to be transmitted to the processor module; and the processor module stores a preset test standard and compares and calculates the feedback information according to the preset test standard so as to determine whether the driver has the risky driving behavior.

In order to solve the above-mentioned technical problem, the present invention further provides an electronic device including a memory, a processor and a computer program stored in the memory and running on the processor, wherein the above-mentioned risky driving prediction method based on the brain-computer interface or the above-mentioned risky driving prediction system based on the brain-computer interface is implemented when the computer program is executed by the processor.

According to the risky driving prediction method, risky driving prediction system and electronic device provided by the present invention, a prediction mechanism for a risky driving behavior of a driver is formed by virtue of an interactive application of a brain-computer interface technology and a test item set to directly, accurately and objectively detect whether the driver currently has the responsiveness and judgment suitable for driving a vehicle without requiring the driver to do any body movement or language response, so that harm caused by the risky driving behavior of the driver is avoided.

Figure 1:
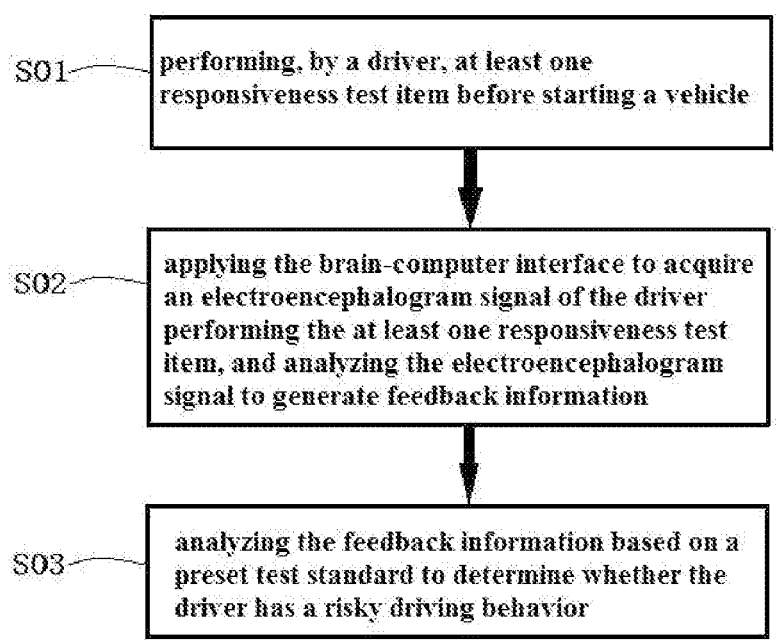
FIG. 1 is a step process diagram of a risky driving prediction method based on a brain-computer interface according to the present invention.

DESCRIPTION FOR REFERENCE NUMERALS IN THE ACCOMPANYING DRAWINGS steps S01 to S03; driver A; test module 1; information acquisition and analysis module 2; electroencephalogram signal extraction interface 21; signal pre-processing unit 22; signal feature extraction unit 23; feature analysis unit 24; data transmission unit 25; analysis server 26; and processor module 3.

DETAILED DESCRIPTION OF THE INVENTION

Detailed descriptions and technical contents of the present invention will be shown as follows in cooperation with the accompanying drawings. However, the attached accompanying drawings are merely for reference and description purposes, but are not intended to limit the present invention. Shown by relevant research results, in the morning after a person is drunk as a lord, he may still have hangover symptoms such as vertigo and headache, fatigue and weakness and difficulty in focusing the attention even if the blood alcohol concentration (BAC) in the body is reduced to zero, and then, the judgement and responsiveness of a driver in driving are affected, which makes the driver incapable of appropriately controlling a vehicle, and thus, a risky driving behavior is caused. However, compared with the risk of drunk driving, the high risk of driving in the next day after the hangover is easily neglected by people, and a risky driving state of the driver in the next day after the hangover cannot be detected at all by applying an existing monitoring instrument such as an expiratory alcohol detector, a spatial alcohol content monitor and a sweat component analyzer. In addition, when the driver suffers from aypnia, is overfatigued and takes drugs with greater side effects or forbidden drugs, the risky driving behavior of the driver may also be caused even if he does not drink.

The present invention is intended to determine whether a driver has the judgement and responsiveness suitable for driving a vehicle before driving a vehicle by virtue of a direct technical means, and such a determination mechanism may not be affected by external factors (such as change of an alcohol concentration in a body) and is capable of accurately determining the lowering of judgement and responsiveness caused by aypnia, overfatigue and drug influences. Specifically, the present invention provides a risky driving prediction method and system based on a brain-computer interface, and an electronic device. A BCI (Brain Computer Interface) technology on which the present invention is based is a technology for achieving information interaction between a brain and a device by creating a direct connecting channel between the brain of a person or an animal and an external device, and at present, this technology has been applied in fields such as exercise rehabilitation and neural interference. The BCI technology is a brand new information exchange and control technology mainly achieved by acquiring and analyzing brain neural signals in different states and recognizing the brain neural signals to establish the direct information exchange and control channel between the brain and the external device. The BCI technology may be used for directly expressing willingness or operating the external device by outputting the brain neural signals without language or actions or an input/output apparatus such as a keyboard, a mouse and a camera. A brain in the BCI technology refers to a brain or neural system in a form of an organic life; a computer refers to a device having processing or computing ability and may be in a specific form of an implantable chip or an external wearable device or a combination of the both; and an interface refers to a mediator for information interaction and may be a software program or a hardware chip or a circuit, the interface serving as an important component is used for information conversion between the brain neural signals and the external device, on one hand, the interface may be used for extracting the brain neural signals from brain nerves to recognize and process contents of intentions, and on the other hand, the interface may convert external information or signals into the brain neural signals and input the brain neural signals to brain neural cells to stimulate the brain to generate perception, thereby forming information feedback to the brain. As for the present invention, in a possible implementation manner, the adopted interface is a non-intrusive interface, that is, a wearable device such as an electroencephalogram cap and an electroencephalogram helmet and only needs to acquire and analyze the brain neural signals to recognize the intentions, rather than to convert external information or signals into the brain neural signals to be input to the brain neural cells. In other feasible implementation manners, the interface may also be intrusive, that is an electrode is directly implanted to a cerebral cortex in a manner such as surgery, and thus, high-quality neural signals may be achieved; and the interface may be semi-intrusive, that is, a BCI is implanted to a cranial cavity, but such a manner is mainly used for information analysis based on electrocorticogram (ECoG) outside the cerebral cortex.

As shown in FIG. 1 which is a step process diagram of a risky driving prediction method based on a BCI according to the present invention, the risky driving prediction method includes the steps.

Step S01: a driver performs at least one responsiveness test item before starting a vehicle.

Step S02: a BCI is applied to acquire an electroencephalogram signal of the driver performing the at least one responsiveness test item, and the electroencephalogram signal is analyzed to generate feedback information.

Step S03: the feedback information is analyzed based on a preset test standard to determine whether the driver has a risky driving behavior.

The electroencephalogram signal in the risky driving prediction method is a brain neural signal generated by the brain when the driver performs the responsiveness test item. The responsiveness test item is a stimulus for at least one of the driver's visual or auditory senses, the stimulus may be to play a section of video image for simulating driving or play a section of voice prompt for the driver, so that a brain neural signal of the video image and/or voice prompt is generated in the brain of the driver and is acquired and analyzed by the BCI to generate feedback information. The feedback information includes intentions actually generated by the driver when performing the responsiveness test item and starting time of generating the intentions. For example, when a section of video image (the responsiveness test item) of a left-turning road is played, this intention is a left-turning intention generated by the driver, and the starting time of generating the intention is the time when the left-turning intention is generated, for example, the driver generates the left-turning intention within 0.2 s after the video image of the left-turning road is played. The preset test standard includes correct intentions supposed to be generated by the driver when performing the responsiveness test item and a time threshold of generating the correct intentions. For example, when a section of video image (the responsiveness test item) of a left-turning road is played, this correct intention is to turn left, and the time threshold is the time when the left-turning intention should be generated within 0.3 s after the video image of the left-turning road is played. Herein, it should be noted that the above-mentioned starting time 0.2 s and time threshold 0.3 s are merely used for illustration, the time threshold is obtained by calculating a great number of normal values of a specific responsiveness test item, the content of the responsiveness test item may be a video image for simulating turning road, or a video image for simulating emergency braking in a special situation (for example, a pedestrian suddenly runs into a front driving route), or a pure voice prompt instruction or a combination of other video images and voice prompt instructions, which is not limited in the present invention. In an actual application, a possible implementation manner for affirming whether the intentions generated by the driver are the correct intentions is to model a relationship between each of different modes of neural activities and an expected movement direction so as to construct a calibration decoder for predicting a direction or speed of a movement which is to occur or expected. For example, if the correct intentions which should be generated by the driver are to uplift the right foot placed on the accelerator, move the right foot according to a correct direction and press on the brake in a responsiveness test item, it should be noted that these actions do not need to be actually made by the driver, it is enough for the driver to imagine such operations in the mind after seeing the responsiveness test item, that is, cross-space mind control is only needed. It is easily understood that the correct intentions mentioned herein may be an action combination synthesized by a plurality of actions according to a correct order; in correspondence to each action intention, it is certain that the discharge rate of a corresponding neuron may be obviously increased; and the pulse on each electrode is automatically detected according to a preset algorithm running on the BCI, next, the discharge rate of a motoneuron corresponding to each electrode in a responsiveness test is analyzed, then, the neural signal is decoded, and thus, it may be further determined whether the intentions generated by the driver are the correct intentions. It should be further explained that the starting time of generating the intentions may be set as a moment when the discharge rates of neurons corresponding to the intentions are suddenly changed by one preset growing rate. In the above-mentioned steps S01 to S03, in some possible embodiments, the driver may also a safety officer driving a L4-grade unmanned vehicle.

Figure 2:
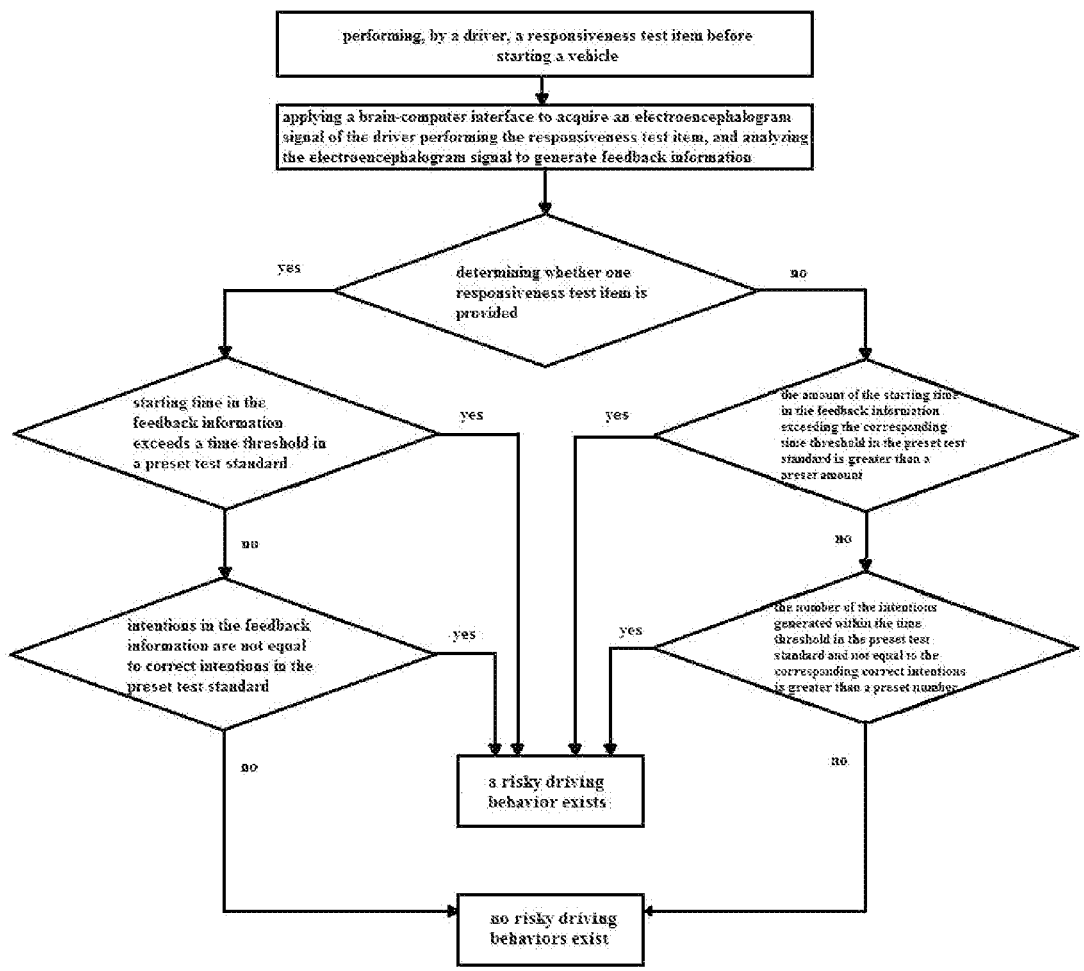
FIG. 2 is a process diagram for analysis and determination whether a driver has a risky driving behavior in the present invention.

As shown in combination with FIG. 2, a specific process for analyzing and determining whether the driver has the risky driving behavior in the risky driving prediction method is that: when one responsiveness test item is provided, if the starting time exceeds the time threshold or the intentions generated within the time threshold are not equal to the correct intentions, it is determined that the driver has the risky driving behavior; and when a plurality of responsiveness test items are provided, if the amount of the starting time exceeding the corresponding time threshold is greater than a preset amount or the number of the intentions generated within the time threshold and not equal to the corresponding correct intentions is greater than a preset number, it is determined that the driver has the risky driving behavior.

The following table 1 shows three embodiments for describing a process for determining whether the driver has the risky driving behavior when one responsiveness test item is provided, wherein the video image for simulating the emergency braking in the special situation is used as the responsiveness test item, the correct intention in the preset test standard is to brake, and the time threshold is smaller than or equal to 0.2 s.

TABLE 1

|  | Intention | Starting time | Whether the risky driving behavior exists |
| --- | --- | --- | --- |
| Embodiment 1 | Brake | 0.22 s | Yes |
| Embodiment 2 | Not brake | 0.18 s | Yes |
| Embodiment 3 | Brake | 0.15 s | No |

Known from the table 1, in the embodiment 1, although the driver generates a correct intention, the time of generating the correct intention exceeds the time threshold, that is, the responsiveness is delayed, the driver is not suitable for driving the vehicle, and therefore, the risky driving behavior exists; in the embodiment 2, although a response is made within the time threshold, the intention generated by the driver is not the correct intention, that is, incorrect judgement is caused, the driver is not suitable for driving the vehicle, and therefore, the risky driving behavior exists; and in the embodiment 3, the driver generates a correct intention within the time threshold, and therefore, no risky driving behaviors exist.

The following table 2 shows ten embodiments for describing a process for determining whether the driver has the risky driving behavior when four (more) responsiveness test items are provided, wherein four responsiveness test items are respectively: (1) the video image for simulating the emergency braking in the special situation, (2) the video image of the left-turning road, (3) voice prompt for turning left, and (4) a video image, with a voice prompt for deceleration, of a sharp left-turning road; the correct intentions in the preset test standard corresponding to the four responsiveness test items are respectively to: brake, turn left, turn right and brake for deceleration while turning left; the corresponding time thresholds are respectively: ≤0.2 s, ≤0.22 s, ≤0.22 s and ≤0.25 s: and the preset amount is set as 1, and the preset number is set as 1.

TABLE 2

|  | Intention 1 | Starting time 1 | Intention 2 | Starting time 2 | Intention 3 | Starting time 3 | Intention 4 | Starting time 4 | Whether a risky driving behavior exists |
| --- | --- | --- | --- | --- | --- | --- | --- | --- | --- |
| Embodiment 1 | Brake | 0.22 s | Turn left | 0.25 s | Turn right | 0.26 s | Brake for deceleration while turning left | 0.31 s | Yes |
| Embodiment 2 | Not brake | 0.18 s | Not turn left | 0.2 s | Not turn right | 0.19 s | Brake for deceleration while not turning left | 0.23 s | Yes |
| Embodiment 3 | Brake | 0.22 s | Turn left | 0.2 s | Turn right | 0.2 s | Brake for deceleration while turning left | 0.3 s | Yes |
| Embodiment 4 | Brake | 0.18 s | Not turn left | 0.2 s | Turn right | 0.21 s | Brake for deceleration while not turning left | 0.22 s | Yes |

TABLE 2-continued

|  | Intention 1 | Starting time 1 | Intention 2 | Starting time 2 | Intention 3 | Starting time 3 | Intention 4 | Starting time 4 | Whether a risky driving behavior exists |
|---|---|---|---|---|---|---|---|---|---|
| Embodiment 5 | Not brake | 0.21 s | Turn left | 0.2 s | Turn right | 0.2 s | Brake for deceleration while turning left | 0.26 s | Yes |
| Embodiment 6 | Brake | 0.18 s | Not turn left | 0.22 s | Turn right | 0.21 s | Brake for deceleration while not turning left | 0.22 s | Yes |
| Embodiment 7 | Brake | 0.17 s | Not turn left | 0.23 s | Turn right | 0.21 s | Brake for deceleration while turning left | 0.23 s | No |
| Embodiment 8 | Brake | 0.17 s | Not turn left | 0.22 s | Turn right | 0.22 s | Brake for deceleration while turning left | 0.24 s | No |
| Embodiment 9 | Brake | 0.21 s | Turn left | 0.19 s | Turn right | 0.21 s | Brake for deceleration while turning left | 0.22 s | No |
| Embodiment 10 | Brake | 0.2 s | Turn left | 0.2 s | Turn right | 0.21 s | Brake for deceleration while turning left | 0.2 s | No |

Known from table 2, in the embodiment 1, although the driver generates correct intentions, the time of generating the correct intentions exceeds the time threshold, that is, the responsiveness is seriously delayed, and therefore, the risky driving behavior exists; in the embodiment 2, although a response is made within the time threshold, all the intentions generated by the driver are not the correct intentions, that is, fatally incorrect judgement is caused, and therefore, the risky driving behavior exists; in the embodiment 3, the intentions generated by the driver are correct, but starting time of each of two intentions exceeds the time threshold, which proves that the responsiveness of the driver is insufficient, and therefore, the risky driving behavior exists; in the embodiment 4, although the driver makes a response within the time threshold, two of the intentions are incorrect, which proves that the judgement of the driver is insufficient, the risky driving behavior exists; in the embodiment 5, the driver has two overtime intentions and one incorrect intention, which proves that the responsiveness of the driver is insufficient, and therefore, the risky driving behavior exists; in the embodiment 6, the driver has two incorrect intentions, which proves that the judgement of the driver is insufficient, and therefore, the risky driving behavior exists; in the embodiment 7, although the driver has one overtime intention and one incorrect intention, the number of non-conforming items is not greater than the preset amount and the present number which are both 1, which proves that the driver has a certain responsiveness and judgement to be able to drive a vehicle, and therefore, no risky driving behaviors exist; in the embodiments 8 and 9, the driver respectively has one incorrect intention and one overtime intention which are within an allowable range, and therefore, no risky driving behaviors exist; and in the embodiment 10, the intentions generated by the driver within the time threshold are all correct, and therefore, no risky driving behaviors exist. During actual implementation, in order to more accurately detect the responsiveness and judgement of the driver, the number of the responsiveness test items may be appropriately increased. In addition, in order to strictly control the risky driving behavior of the driver, the situation that the responsiveness of the driver is lagged or the judgement of the driver is lowered is not allowed, and the preset amount and the preset number may also be set as zero.

Figure 3:
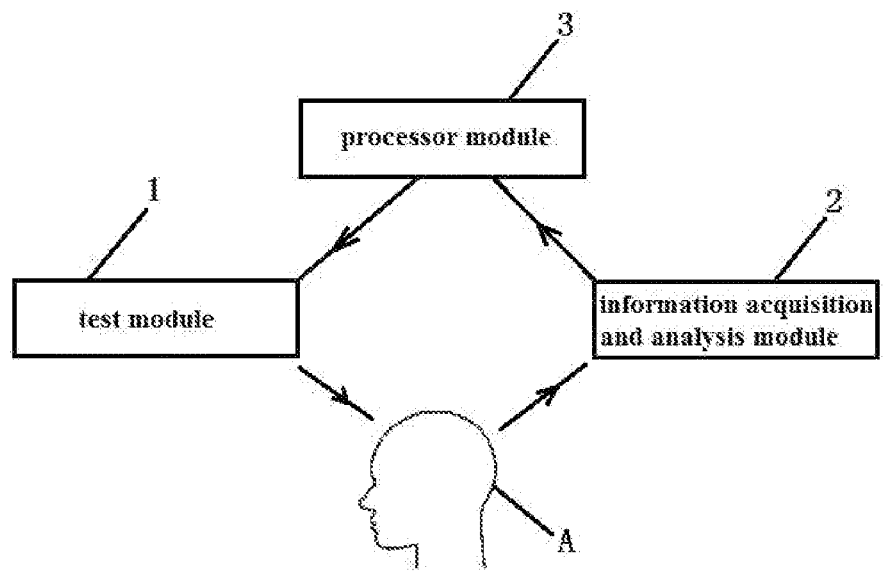
FIG. 3 is a schematic diagram of functional modules of a risky driving prediction system based on a brain-computer interface according to the present invention.

As shown in FIG. 3 which is a schematic diagram of functional modules of a risky driving prediction system based on a BCI according to the present invention, the risky driving prediction system includes a test module 1, an information acquisition and analysis module 2 and a processor module 3, wherein each of the test module 1 and the information acquisition and analysis module 2 is electrically connected with the processor module 3; the test module 1 acquires a responsiveness test item and test interaction information of a driver A by virtue of the processor module 3 so as to test the driver A; the information acquisition and analysis module 2 acquires an electroencephalogram signal of the driver A being tested and analyzes the electroencephalogram signal so as to generate feedback information to be transmitted to the processor module 3; and the processor module 3 stores a preset test standard and compares and calculates the feedback information according to the preset test standard so as to determine whether the driver A has the risky driving behavior.

In correspondence to the above-mentioned risky driving prediction method, the test module 1 displays and/or plays the responsiveness test item consisting of images (video images) and/or voice (voice prompt) for the driver A, and the test module 1 may include a vehicle-mounted head-up display apparatus, a vehicle-mounted center control display apparatus or a mobile device held by the driver. The running time of the responsiveness test item is recorded by the processor module 3, and the processor module 3 compares and calculates intentions in the feedback information and starting time of generating the intentions according to correct intentions and a time threshold corresponding to the responsiveness test item in the preset test standard so as to determine whether the driver A has the risky driving behavior. In addition, the processor module 3 may also convert the intentions into the test interaction information to be displayed and/or played in the responsiveness test item displayed and/or played by the test module 1. For example, the steering wheel in the video image of the left-turning road displayed in the test module 1 may be displayed to be steered leftwards according to the intention of the driver A who wants to turn left. In correspondence to the above-mentioned risky driving prediction method, a specific operation process that the feedback information is compared and calculated according to the preset test standard may be performed in the processor module 3. When one responsiveness test item is provided, if it is calculated by the processor module 3 that the starting time exceeds the time threshold or the intentions generated within the time threshold are not equal to the correct intentions, it is determined that the driver A has the risky driving behavior; and when a plurality of responsiveness test items are provided, if it is calculated by the processor module 3 that the amount of the starting time exceeding the corresponding time threshold is greater than a preset amount or the number of the intentions generated within the time threshold and not equal to the corresponding correct intentions is greater than a preset number, it is determined that the driver A has the risky driving behavior.

Figure 4:
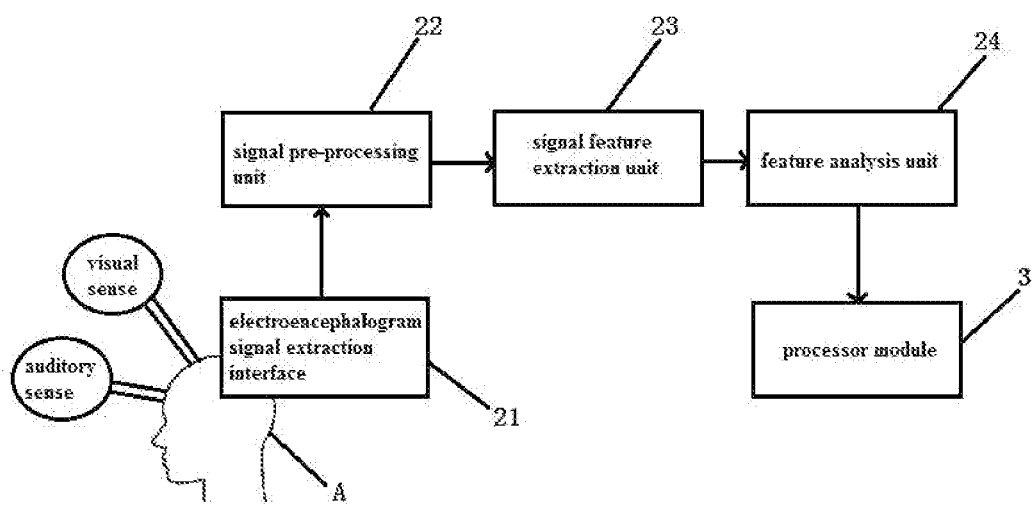
FIG. 4 is a schematic diagram of functional modules in an implementation manner of an information acquisition and analysis module in the present invention.

More specifically, as shown in FIG. 4, the information acquisition and analysis module 2 includes an electroencephalogram signal extraction interface 21, a signal pre-processing unit 22, a signal feature extraction unit 23 and a feature analysis unit 24. The electroencephalogram signal extraction interface 21 is used for acquiring a brain neural signal (that is, the electroencephalogram signal) of the driver A being tested and may be worn on the head of the driver A by a wearable device; the signal pre-processing unit 22 is used for performing filtration and amplified signal processing on the brain neural signal; the signal feature extraction unit 23 is used for extracting a signal feature of the brain neural signal subjected to filtration and amplified signal processing; and the feature analysis unit 24 is used for processing the signal feature by virtue of a machine learning model to generate feedback information.

Figure 5:
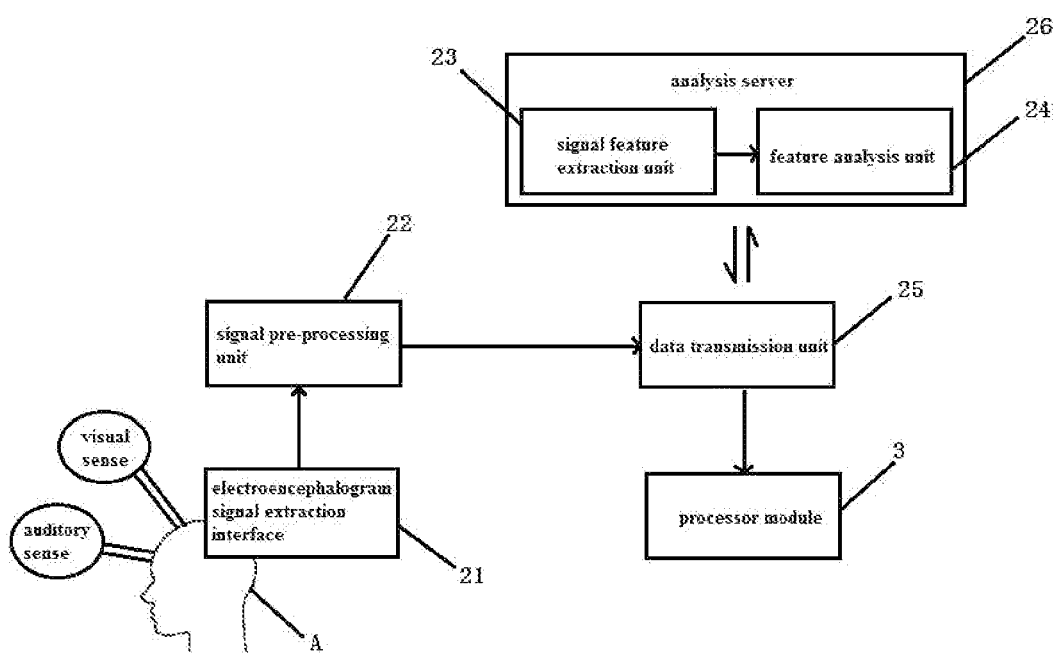
FIG. 5 is a schematic diagram of functional modules in another implementation manner of the information acquisition and analysis module in the present invention.

In order to relieve the processing burden of the information acquisition and analysis module 2, as another implementation manner of the risky driving prediction system provided by the present invention, as shown in FIG. 5, the information acquisition and analysis module 2 may further include a data transmission unit 25 and an analysis server 26. The signal feature extraction unit 23 and the feature analysis unit 24 of the information acquisition and analysis module 2 are arranged on the analysis server 26; the data transmission unit 25 is electrically connected with the processor module 3 and is connected with the analysis server 26 in a wired or wireless data transmission manner; and the brain neural signal subjected to filtration and amplified signal processing is transmitted to the signal feature extraction unit 23 located on the analysis server 26 by the data transmission unit 25 so as to be subjected to signal feature extraction, and the signal feature is processed by the feature analysis unit 24 located on the analysis server 26 by virtue of the machine learning model to generate the feedback information and is transmitted to the processor module 3 by the data transmission unit 25. Therefore, a signal feature extraction link and a signal feature analysis link having greater operation and processing amounts are processed under the support of the remote analysis server 26 having stronger operation and processing abilities, so that the processing burden of the local information acquisition and analysis module 2 is relieved, and then, the running efficiency of the system is increased. In addition, the processor module 3 may also update the preset test standard and the responsiveness test item by virtue of the data transmission unit 3.

As a supplement of the risky driving prediction system based on the BCI in the present invention, the risky driving prediction system may further include a behavior response detection module (not shown in the figure). The behavior response detection module is not based on the BCI technology, but is a module for determining the responsiveness of limbs of a driver. The behavior response detection module consists of several sensors electrically connected with the processor module, and the several sensors are respectively arranged on an actuating system and a steering system of a vehicle; when the driver is tested by the test module, the driver controls the actuating system or the steering system to do a behavior action relevant to the responsiveness test item, and meanwhile, the processor module acquires the running time of the responsiveness test item as well as sensing signals and sensing time of the sensors; and the processor module compares and calculates the sensing signals and the sensing time according to correct sensing signals and a sensing time threshold corresponding to the responsiveness test item in the preset test standard so as to help to determine whether the driver has the risky driving behavior.

In addition, in many countries, a drunk driving behavior is classified as a violation or unlawful behavior, and once a driver drinks, his driving behavior will become the risky driving behavior. Moreover, shown by a result of a vehicle collision experiment from Tsinghua University in China, if a driver drives a vehicle at the speed of 60 km/h, the braking distance achieved after the driver drinks is 50 m to 119 m, but if the driver does not drink, the braking distance is only 31 m to 53 m, by performing comparison before and after the driver drinks, it can be seen that the maximum braking distance may reach more than 50 m, by which harm caused by drinking is apparent. Therefore, as another supplement of the risky driving prediction system based on the BCI in the present invention, the risky driving prediction system may further include a blood alcohol concentration detection module (not shown in the figure). The blood alcohol concentration detection module is not based on the BCI technology, too, but is used to measure an alcohol concentration by contact with a body part of a driver. Specifically, the blood alcohol concentration detection module is electrically connected with the processor module and is provided with a contact-type optical detection sensor, the contact-type optical detection sensor is in contact with a body part of the driver, for example, the contact-type optical detection sensor is arranged on a steering wheel to be in contact with a palm of the driver, thereby measuring the alcohol concentration in the body of the driver. The blood alcohol concentration detection module transmits the alcohol concentration to the processor module, and the processor module compares and calculates the alcohol concentration according to an alcohol concentration threshold in the preset test standard so as to help to determine whether the driver has the risky driving behavior.

As further supplement of the risky driving prediction system based on the BCI in the present invention, the risky driving prediction system may further include a vehicle starting unlocking module (not shown in the figure). The vehicle starting unlocking module is electrically connected with the processor module and a vehicle ignition system respectively, and when the processor module determines that the driver has the risky driving behavior, the processor module controls the vehicle starting unlocking module to shut down the vehicle ignition system.

In addition to the above-mentioned risky driving prediction method and system based on the BCI, the present invention further provides an electronic device and a non-transitory computer readable storage medium. The electronic device includes a memory, a processor and a computer program stored in the memory and running on the processor, wherein the above-mentioned risky driving prediction method based on the BCI or the above-mentioned risky driving prediction system based on the BCI is implemented when the computer program is executed by the processor. The non-transitory computer readable storage medium stores a computer program, wherein the above-mentioned risky driving prediction method based on the BCI or the above-mentioned risky driving prediction system based on the BCI is implemented when the computer program is executed by the processor.

The above descriptions are merely preferred embodiments of the present invention, but are not intended to limit the patent scope of the present invention. Other equivalent variations made by applying the patent conception of the present invention shall fall within the patent protection scope of the present invention.

The invention claimed is:

1. A risky driving prediction method based on a brain-computer interface, comprising:
   performing, by a driver, at least one responsiveness test item before staffing a vehicle, wherein the at least one responsiveness test item includes one or more of playing a section of a video image for simulating driving or playing a section of a voice prompt with driving instructions for the driver;
   applying a brain-computer interface to acquire an electroencephalogram signal of the driver performing the at least one responsiveness test item, and analyzing the electroencephalogram signal to generate feedback information, the feedback information comprises intentions actually generated by the driver when performing the responsiveness test item and starting time of generating the intentions;
   based on a preset test standard that comprises correct intentions supposed to be generated by the driver when performing the responsiveness test item and a time threshold of generating the correct intentions, wherein when one responsiveness test item is provided, if the starting time exceeds the time threshold or the intentions generated within the time threshold are not equal to the correct intentions, it is determined that the driver has the risky driving behavior;
   when a plurality of responsiveness test items are provided, if the amount of the starting time exceeding the corresponding time threshold is greater than a preset amount or the number of the intentions generated within the time threshold and not equal to the corresponding correct intentions is greater than a preset number, it is determined that the driver has the risky driving behavior; and
   further comprising a vehicle starting unlocking module, wherein the vehicle starting unlocking module is electrically connected with the processor module and a vehicle ignition system respectively, and when the processor module determines that the driver has the risky driving behavior, the processor module controls the vehicle starting unlocking module to shut down the vehicle ignition system.

2. The risky driving prediction method of claim 1, wherein the responsiveness test item is a stimulus for at least one of the driver's visual or auditory senses.

3. An electronic device, comprising a memory, a processor and a computer program stored in the memory and running on the processor, wherein the risky driving prediction method based on a brain-computer interface of claim 1 is implemented when the computer program is executed by the processor.

4. A risky driving prediction system based on a brain-computer interface, comprising a test module, an information acquisition and analysis module and a processor module, wherein each of the test module and the information acquisition and analysis module is electrically connected with the processor module; the test module is configured to acquire a responsiveness test item composed of images and/or sounds for simulating driving, as well as test interaction information of a driver by virtue of the processor module, so as to display and/or play the responsiveness test item to test the driver; the information acquisition and analysis module is configured to acquire an electroencephalogram signal of the driver being tested and analyze the electroencephalogram signal so as to generate feedback information to be transmitted to the processor module; and the processor module is configured to store a preset test standard and record a running time of the responsiveness test item, as well as compares intentions in the feedback information and starting time of generating the intentions according to correct intentions and a time threshold corresponding to the responsiveness test item in the preset test standard, wherein when one responsiveness test item is provided, the processor module is configured to compare the starting time exceeds the time threshold or the intentions generated within the time threshold are not equal to the correct intentions, it is determined that the driver has the risky driving behavior; and wherein when a plurality of responsiveness test items are provided, the processor module is configured to compare the amount of the starting time exceeding the corresponding time threshold is greater than a preset amount or the number of the intentions generated within the time threshold and not equal to the corresponding correct intentions is greater than a preset number, it is determined that the driver has the risky driving behavior; and
   further comprising a vehicle starting unlocking module, wherein the vehicle starting unlocking module is electrically connected with the processor module and a vehicle ignition system respectively, and when the processor module determines that the driver has the risky driving behavior, the processor module controls the vehicle starting unlocking module to shut down the vehicle ignition system.

5. The risky driving prediction system of claim 4, wherein the processor module is configured to can also convert the intentions into the test interaction information to be displayed and/or played in the responsiveness test item displayed and/or played by the test module.

6. The risky driving prediction system of claim 4, wherein the test module comprises a vehicle-mounted head-up display apparatus, a vehicle-mounted center control display apparatus or a mobile device held by the driver.

7. The risky driving prediction system of claim 4, wherein the information acquisition and analysis module comprises an electroencephalogram signal extraction interface, a signal pre-processing unit, a signal feature extraction unit and a feature analysis unit; the electroencephalogram signal extraction interface is configured to acquire a brain neural signal of the driver being tested; the signal pre-processing unit is configured to perform filtration and amplify signal processing on the brain neural signal; the signal feature extraction unit is configured to extract a signal feature of the brain neural signal subjected to filtration and amplified signal processing; and the feature analysis unit is configured to process the signal feature by virtue of a machine learning model to generate feedback information.

8. The risky driving prediction system of claim 7, wherein the information acquisition and analysis module further comprises a data transmission unit and an analysis server; the signal feature extraction unit and the feature analysis unit of the information acquisition and analysis module are arranged on the analysis server; the data transmission unit is electrically connected with the processor module and is connected with the analysis server in a wired or wireless data transmission manner; and the brain neural signal subjected to filtration and amplified signal processing is transmitted to the signal feature extraction unit located on the analysis server by the data transmission unit so as to be subjected to signal feature extraction, and the signal feature is processed by the feature analysis unit located on the analysis server by virtue of the machine learning model to generate the feedback information and is transmitted to the processor module by the data transmission unit.

9. The risky driving prediction system of claim 8, wherein the processor module further updates the preset test standard and the responsiveness test item by virtue of the data transmission unit.

10. The risky driving prediction system of claim 4, further comprising a blood alcohol concentration detection module, wherein the blood alcohol concentration detection module is electrically connected with the processor module to detect an alcohol concentration of blood of the driver so as to determine whether the driver has the risky driving behavior.

11. The risky driving prediction system of claim 10, wherein the blood alcohol concentration detection module is provided with a contact-type optical detection sensor, the contact-type optical detection sensor measures the alcohol concentration by contact with a body part of the driver and transmits the alcohol concentration to the processor module, and the processor module compares the alcohol concentration according to an alcohol concentration threshold in the preset test standard so as to help to determine whether the driver has the risky driving behavior.

12. An electronic device, comprising a memory, a processor and a computer program stored in the memory and running on the processor, wherein the risky driving prediction system of claim 4 is implemented when the computer program is executed by the processor.

* * * * *